United States Patent
Kadash et al.

(10) Patent No.: US 6,235,964 B1
(45) Date of Patent: May 22, 2001

(54) WOUND DRESSING

(75) Inventors: Marjory A. Kadash, Skillman; Thomas P. Marsh, Ewing, both of NJ (US); Salina Smith, Chalfont, PA (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/256,140

(22) Filed: Feb. 24, 1999

Related U.S. Application Data

(62) Division of application No. 08/722,331, filed on Sep. 27, 1996, now Pat. No. 5,897,516.

(51) Int. Cl.$^7$ ............................................. A61F 13/00
(52) U.S. Cl. ............................... 602/41; 602/42; 602/47
(58) Field of Search ........................ 602/41, 42, 47, 602/52, 58

(56) References Cited

U.S. PATENT DOCUMENTS

| | | |
|---|---|---|
| 2,273,873 | 2/1942 | Klein . |
| 2,337,011 | 12/1943 | Young . |
| 2,632,443 | 3/1953 | Lesher . |
| 3,425,412 | 2/1969 | Pope . |
| 3,675,654 | 7/1972 | Baker et al. . |
| 4,181,127 | 1/1980 | Linsky et al. . |
| 4,334,530 | 6/1982 | Hassell . |
| 4,541,426 | 9/1985 | Webster . |
| 4,561,435 | 12/1985 | McKnight et al. . |
| 4,742,826 | 5/1988 | McLorg . |
| 4,786,282 | 11/1988 | Wagle et al. . |
| 4,832,009 | 5/1989 | Dillon . |
| 4,917,112 | 4/1990 | Kalt . |
| 5,000,172 | 3/1991 | Ward . |
| 5,018,515 | 5/1991 | Gilman . |
| 5,056,510 | 10/1991 | Gilman . |
| 5,181,905 | 1/1993 | Flam . |
| 5,244,457 | 9/1993 | Karami et al. . |
| 5,250,043 | * 10/1993 | Castellana . |
| 5,264,218 | 11/1993 | Rogozinski . |
| 5,265,605 | 11/1993 | Afflerbach . |
| 5,270,358 | 12/1993 | Asmus ................................... 524/55 |
| 5,310,402 | 5/1994 | Rollband . |
| 5,354,261 | 10/1994 | Clark et al. . |
| 5,395,675 | 3/1995 | Altholz et al. . |
| 5,423,737 | 6/1995 | Cartmell et al. . |
| 5,476,443 | 12/1995 | Cartmell et al. . |
| 5,489,262 | 2/1996 | Cartmell et al. . |
| 5,501,661 | 3/1996 | Cartmell et al. . |
| 5,951,505 | * 9/1999 | Gilman et al. . |

FOREIGN PATENT DOCUMENTS

| | | |
|---|---|---|
| 0768071 | 4/1997 | (EP) . |
| 0876809 | 11/1998 | (EP) . |
| 9912581 | 3/1999 | (WO) . |

* cited by examiner

*Primary Examiner*—Michael A. Brown
*Assistant Examiner*—Lalita M. Hamilton
(74) *Attorney, Agent, or Firm*—Theodore R. Furman, Jr.; John M. Kilcoyne

(57) ABSTRACT

An improved wound dressing is provided which comprises a backing layer bearing a reference marking, a hydrocolloid layer and a release layer. The hydrocolloid swells in use. This swelling can be seen or felt through the backing layer. When the swelling extends to or beyond the reference marking, the dressing should be changed to prevent leaking. Thus, the dressing can be left in place for as long as possible, but not so long as to damage the underlying skin.

3 Claims, 2 Drawing Sheets

WOUND DRESSING

This application is a divisional of application Ser. No. 08/722,331 filed on Sep. 27, 1996 now U.S. Pat. No. 5,897,516.

FIELD OF THE INVENTION

The present invention relates to a wound dressing that is useful for the treatment of wounds.

BACKGROUND OF THE INVENTION

In connection with the care and treatment of wounds herein, the term "wound" is meant to include chronic wounds such as pressure ulcers (Stage I–IV) and leg ulcers, acute wounds such as surgical wounds (e.g., post operative wounds), traumatic wounds such as minor abrasions and lacerations, burns (first and second degree), punctures, Moh's surgery, dermatological excisions, and the like. A critical aspect of wound care is the consideration of the requirements of the epithelium, i.e., that area of new cell growth over the wound which is formed during the healing process, so that healing is facilitated. Another consideration in wound care is the needs of the surrounding unwounded skin.

Since it is recognized that healing of the wound occurs as the epithelium migrates by growth generally from the periphery inward, care is taken not to damage unnecessarily or to irritate this new area of growth or existing compromised tissue. Frequently, with prior art dressings, problems can occur when dressings are left on a wound for too long a period of time and during dressing changes. For example, dressings can adhere to the epithelium, and granulation tissue and new cell growth can become intertwined within the matrix of the dressings. In these instances, there is a risk that removal of the dressing will damage the sensitive tissue and new growth thereby causing a regression in the progress of wound healing.

Accordingly, another critical consideration in wound care is the frequency of dressing changes. It may be desirable to change dressings frequently when the wound is emitting a large volume of exudate, and less frequently when the wound is emitting less exudate. Nevertheless, each time the dressing is changed, there is a risk that the sensitive tissue and new growth will be unnecessarily damaged. Additionally, positive growth factors in wound fluid might be unnecessarily removed from the wound bed thereby preventing their positive effects. Therefore, it is important to change the dressings when appropriate but not so often as to unnecessarily damage the sensitive tissue and new growth, or to remove the positive growth factors unnecessarily.

Unfortunately, most prior art dressings rely on the caretaker or the patient to decide if a dressing should be changed. In particular in the case of a non-health care professional or the patient alone, it can be difficult to know when a dressing should be changed. For example, one type of wound treatment presently used, in particular for leg ulcers, comprises the application of gauze to the ulcer and the utilization of a compression wrap to secure the gauze to the ulcer. The caretaker essentially must simply guess when it is appropriate to change the dressing. If the dressing is changed too frequently, the underlying tissue can be damaged and part of the useful life of the dressing is wasted. However, if the gauze is left on for too long a period of time, wound exudate can begin to overly hydrate and macerate the patient's surrounding skin.

Some dressings have been made which provide means for monitoring the condition of the underlying skin or wound. For example, a dressing is disclosed in U.S. Pat. No. 5,181,905. This dressing is preferably provided with an electrical-mechanical indicator means capable of sensing the condition of the underlying skin or wound. This indicator is a series of temperature sensitive, color responsive encapsulated liquid crystals.

Other bandages with indicators exist as well such as the bandage shown in U.S. Pat. No. 3,675,654. This bandage includes an absorbent pad disposed on a translucent backing sheet of water impervious material. A moisture-actuated indicating agent is positioned between the pad and the backing sheet. The indicating agent is a small amount of water-soluble dye. When the absorbent pad and the indicating agent become wet in use, the resulting solution between the pad and the backing sheet is visible through the backing sheet to provide an indication of wetness. However, an indication of wetness alone is not necessarily enough to indicate that the bandage should be changed. In fact, if the bandage were changed every time any wetness occurred, the bandage may be being changed too frequently and there is the risk that the sensitive tissue and new cell growth are being damaged each time.

Markings have also been provided on bandages, for example, to indicate the appropriate direction for removal of the bandage from a patient's skin to minimize damage to the underlying healing wound (see, e.g., U.S. Pat. No. 4,334,530), to monitor the size reduction of the wound (see, e.g., U.S. Pat. No. 5,000,172) and to mark the optimum spot for applying pressure to stop bleeding (see, e.g., U.S. Pat. No. 5,310,402).

Nevertheless, considering the various types of wounds, the numerous dressings that are available, and the various stages of healing, there remains a need for a dressing that minimizes premature dressing changes, particularly by the non-health care professional, and thereby optimizes the life of the bandage and yet works to prevent damage to surrounding skin, tissue and new cell growth by frequent dressing changes.

SUMMARY OF THE PRESENT INVENTION

Therefore, in accordance with the present invention, there is provided an improved wound dressing. The dressing comprises a backing layer bearing a reference marking, a hydrocolloid layer and a release layer or delivery system. In operation, the dressing is placed over a wound. The wound emits exudate which is taken up by the hydrocolloid layer, and the hydrocolloid layer swells. In a preferred embodiment, as the hydrocolloid layer swells, it turns white. This swelling can be seen or felt through the backing layer. When the swelling extends to or beyond the reference marking, the dressing should be changed. Thus, the dressing can be left in place for as long as possible, but not so long as to damage the underlying skin by frequent dressing changes, or to risk leaking. In this way, the wound dressing of the present invention provides superior wound care in that the number of dressing changes is minimized and the risk of damaging delicate healing skin peripheral to the wound from frequent dressing changes is minimized. Moreover, the risk of leakage is minimized, the overall wound dressing management, particularly for the non-health care professional, is simplified and the cost of care is reduced.

DETAILED DESCRIPTION OF THE INVENTION

Figure 1:
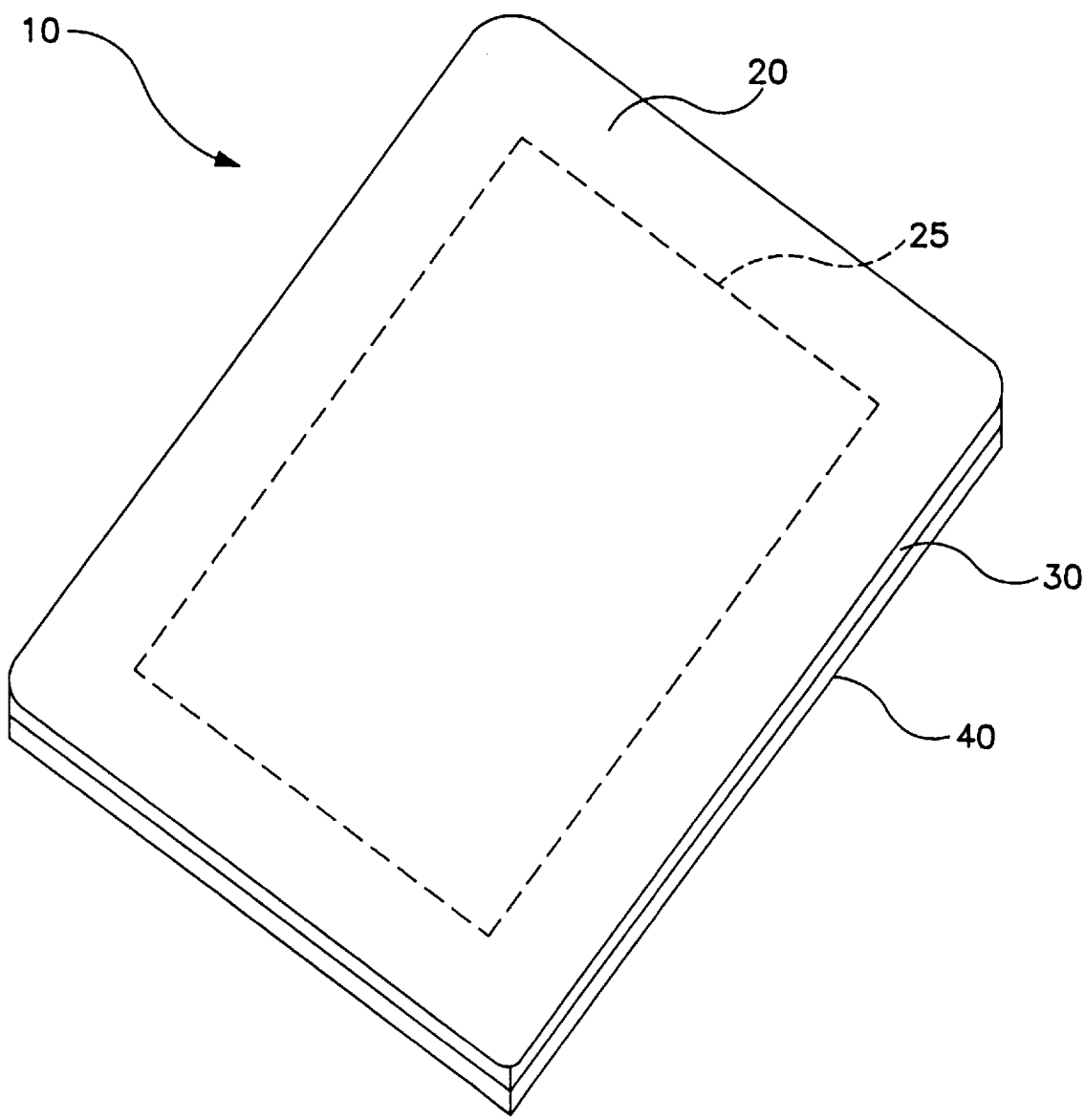
FIG. 1 is a perspective view of one embodiment of the present invention.

Referring to FIG. 1, an embodiment of the wound dressing 10 of the present invention is shown to comprise a backing layer 20 with reference marking 25 which overlies a hydrocolloid layer 30. Release layer 40 is also shown.

The hydrocolloid layer 30 typically comprises fluid interactive adhesives known in the art for the treatment of wounds which emit exudate, and in particular are hydrocolloids dispersed in a polymer matrix (e.g., suspended in an elastomeric matrix). These materials are preferably capable of adhering to moist surfaces.

For example, Chen, in U.S. Pat. No. 3,339,546 discloses an adhesive comprising a blend of one or more water soluble or water swellable hydrocolloids and a viscous substance such as polyisobutylene. A film of water insoluble material, corresponding to the backing layer in the instant case, is affixed to one surface of the adhesive.

Doyle et al., in U.S. Pat. No. 4,551,490, also disclose a pressure sensitive adhesive suitable for use as the hydrocolloid layer in the dressing of the present invention. This adhesive comprises 5 to 30 percent by weight of one or more polyisobutylenes or a blend of one or more polyisobutylenes and butyl rubber, 3 to 20 percent by weight of one or more styrene radial or block type copolymers, 8 to 40 percent by weight of mineral oil, 15 to 65 percent by weight of one or more water soluble hydrocolloid gums, up to 15 percent by weight of one or more water swellable cohesive strengthening agents provided that the hydrocolloid gums and strengthening agents together are present in an amount of between about 15 and 65 percent by weight, and 7.5 to 15 percent by weight of a tackifier.

Preferred for the hydrocolloid layer 30 are the adhesives such as those used in the commercially available products from ConvaTec as Durahesive®, DuoDERM®, DuoDERM® CGF® and Stomahesive®. Nevertheless, while these hydrocolloid layers or adhesives are well suited for use with the present invention, they are merely meant to be exemplary. Any skin compatible hydrocolloid could be employed. Similarly, the hydrocolloid layer can be of any convenient thickness as would be readily understood by those working in the art. For example, the layer can be from approximately 1 mil to 200 mil, preferably from 10 mil to 100 mil, more preferably 20 mil to 50 mil, and especially 35 mil to 45 mil, thick.

In one embodiment of the invention, the hydrocolloid material of the wound dressing may further include adjuvants such as antimicrobial, wound healing and/or odor controlling agents. Further, a color changing additive may be included to facilitate visibility of the hydrocolloid. In particular, a color changing additive may be placed in the hydrocolloid layer to coincide with the reference marking (further discussed below). As the swelling front extends to or beyond the reference marking, the color changing agent may facilitate visibility of the hydrocolloid layer at the reference marking. Other agents typically used in wound care may further be included. For example, between about 2 and 20 percent, and preferably about 10 percent, by weight of zinc oxide can be included in the hydrocolloid material. The zinc oxide not only aids in the care of the skin surrounding the wound, but fluid interactive adhesive materials become more pliable with the zinc oxide included.

The backing layer 20 of the wound dressing is preferably a suitable polymeric material. It can be of any polymer film, nonwoven material, weave or the like, or combination thereof, known in the art. It is preferably made of a thin, flexible, conformable, resilient, supple, limp or flimsy material that can flex or bend to conform to irregular surfaces or contours, such as those of anatomical body parts. The backing layer 20 is preferably transparent or translucent, or it can be opaque. The backing layer 20 can be air permeable to allow oxygen to penetrate the dressing, as well as moisture vapor permeable to allow moisture from the skin surface to escape through the dressing. Additionally, the backing layer 20 can be liquid, air or bacteria impermeable as chosen by those in the art for a particular wound or surface to be treated. A polyurethane layer or polyethylene film is particularly preferred for use as the backing layer in the instant invention.

The backing layer 20 bears a reference marking 25. The reference marking can be presented in any convenient fashion. For example, the reference marking can be printed or embossed on the backing layer, or it can be on a separate layer which can be seen or felt through the backing layer. The reference marking is placed in such a way as to indicate the need to change the dressing. That is, when the absorbed wound exudate extends to or beyond the reference marking, the dressing should be changed. The reference marking can be of any convenient size, shape or conformation depending, for example, on the size and shape of the dressing, the composition and thickness of the hydrocolloid layer, and the wound to be dressed. For instance, the reference marking can consist of a solid line, a semi-solid line, text, shading, symbols or any other configuration. One of ordinary skill in the art would readily be able to place the reference marking in an appropriate location, such as on the backing layer, for example adjacent to the edge of the dressing, to maximize the useful life of the dressing and minimize the need for dressing changes. Of course, in certain circumstances, it may be of value to place the reference markings in a location less than that which would indicate the maximum useful life of the dressing. The invention includes the dressing wherein reference markings are placed in any suitable location.

The release layer 40 can be any convenient release layer or system as known in the art. For example, the layer can comprise, in combination, a siliconized polyester release tab and siliconized release paper.

Figure 2:
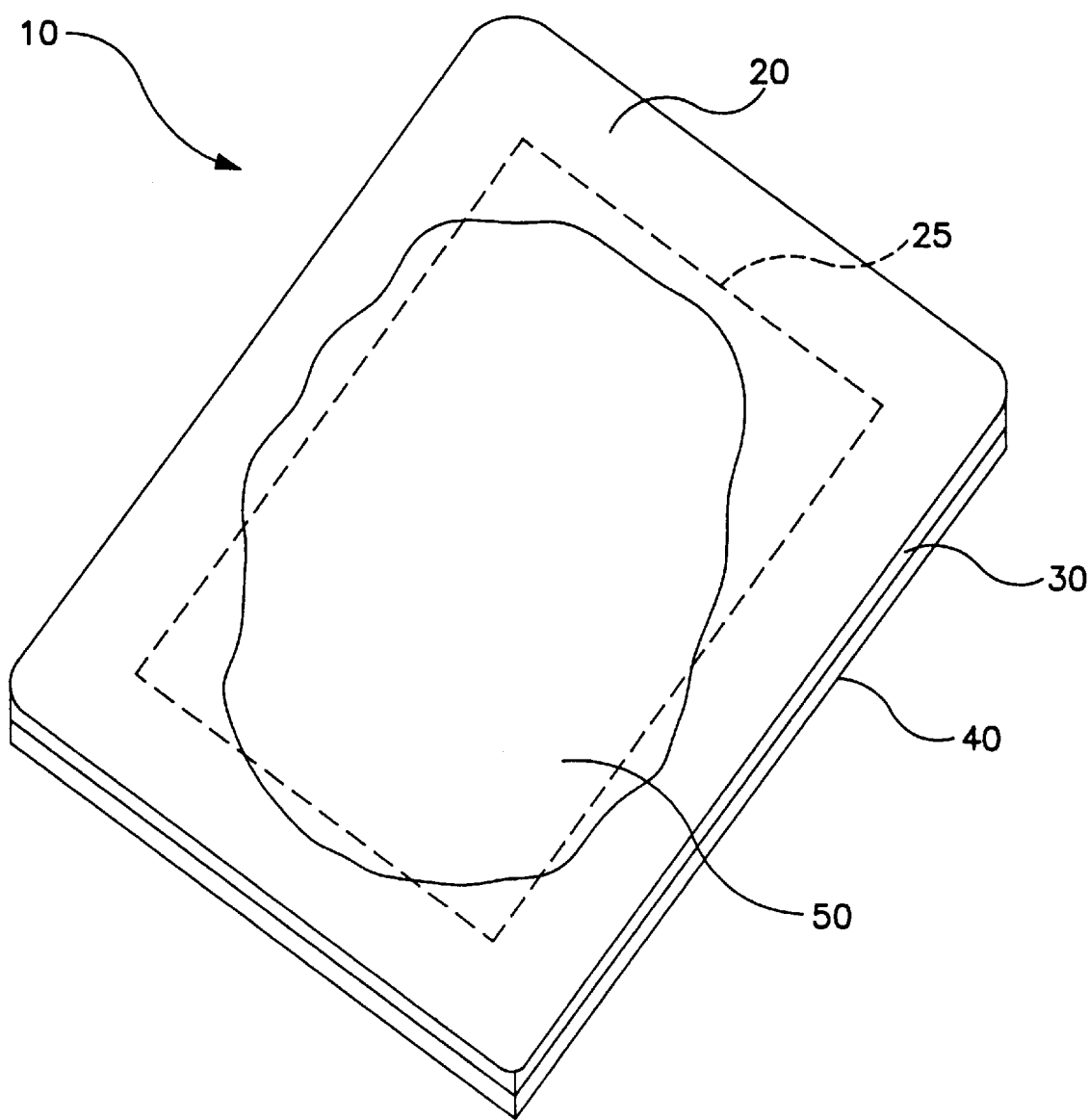
FIG. 2 is a perspective view of the same embodiment of the invention as shown in FIG. 1, when the dressing is ready to be changed.

FIG. 2 represents a perspective view of an embodiment of a wound dressing in accordance with the instant invention when the dressing is ready to be changed. As in FIG. 1, wound dressing 10 is shown with reference marking 25. As the wound emits exudate, the exudate is taken up by the hydrocolloid layer. The hydrocolloid layer swells and, in a preferred embodiment, turns white. (Absent some additional coloring or other agent, hydrocolloids turn white as they are hydrated.) This can be seen through the backing layer. When this swelling 50 extends to or beyond the reference markings 25, the dressing should be changed. In this manner, the dressing is changed so that the maximum life of the dressing is utilized and the surrounding skin, tissue and new cell growth are not disturbed by unnecessarily frequent dressing changes.

The wound dressing 10, and, as discussed above, the reference markings, can be of any convenient size and shape depending on the wound to be dressed. They are depicted as concentric rectangles merely for simplicity.

It will be appreciated by those of ordinary skill in the art that the embodiments shown can be modified without departing from the spirit and scope of the invention.

What is claimed is:

1. A wound dressing comprising a backing layer bearing a reference marking, a hydrocolloid layer and a release layer, wherein said backing layer is a polyurethane layer, said hydrocolloid layer contains a hydrocolloid suspended in an elastomeric matrix, and said reference marking is in a location so that swelling of said hydrocolloid layer extending to or beyond the perimeter of the reference marking indicates that the dressing should be changed.

2. The dressing of claim 1 wherein said reference marking is printed on said backing layer.

3. A wound dressing comprising a backing layer bearing a reference marking, a hydrocolloid layer and a release layer, wherein the reference marking is in a location so that swelling of the hydrocolloid layer extending to or beyond the perimeter of the reference marking indicates that the dressing should be changed, and wherein the wound dressing is opaque.

* * * * *